United States Patent [19]

Israel

[11] Patent Number: 4,668,219
[45] Date of Patent: May 26, 1987

[54] EXPONENTIAL MIXING AND DELIVERY SYSTEM

[76] Inventor: Michael B. Israel, 29 Gann Rd., East Hampton, N.Y. 11937

[21] Appl. No.: 838,244

[22] Filed: Mar. 10, 1986

Related U.S. Application Data

[63] Continuation-in-part of Ser. No. 671,965, Nov. 16, 1984, Pat. No. 4,589,867.

[51] Int. Cl.$^4$ .............................................. A61M 5/00
[52] U.S. Cl. ...................................... 604/85; 604/415
[58] Field of Search ........................... 604/56, 82–85, 604/92, 411–415

[56] References Cited

U.S. PATENT DOCUMENTS

| | | | |
|---|---|---|---|
| 3,993,066 | 11/1976 | Virag | 604/56 X |
| 4,573,967 | 3/1986 | Hargrove et al. | 604/85 X |
| 4,589,867 | 5/1986 | Israel | 604/85 |
| 4,623,334 | 11/1986 | Riddell | 604/85 |

FOREIGN PATENT DOCUMENTS

WO84/03445  9/1984  World Int. Prop. O. ............ 604/85

OTHER PUBLICATIONS

Annals of Internal Medicine (Riddell et al.), 1984, 100:25–28.

Primary Examiner—Dalton L. Truluck
Attorney, Agent, or Firm—Edith T. Grill

[57] ABSTRACT

A nonvented gravity fed exponential mixing and delivery system and apparatus for the administration of a drug in a precalculated manner to give constant therapeutic blood plasma levels in the recipient, (patient), which provides an inexpensive, quick and simple exponential mixing procedure to deliver an infusion containing exponentially decreasing concentrations of a drug, which the exponential mixing of a dilute solution of the drug or isotonic solution which flows by gravity from a conventional IV container, through a coupling means, into a vertically aligned nonvented nondeformable mixing chamber, filled to capacity with a concentrated solution of said drug, said mixing container being provided with a verticle inlet conduit means and a vertical outlet conduit means at opposing ends, each conduit means extending into said mixing container at a height to provide a sufficient height differential to induce exponential mixing of the solutions, to effect an exponentially decreasing concentration of said drug during a constant infusion rate, flowing through said outlet conduit and into a conventional non-vented administration apparatus.

10 Claims, 1 Drawing Figure

EXPONENTIAL MIXING AND DELIVERY SYSTEM

BACKGROUND OF PRIOR ART

This is a continuation-in-part of copending patent application Ser. No. 671,965 filed Nov. 16, 1984 which issued on May 20, 1986 as U.S. Pat. No. 589,867.

The present invention relates to an improved non-vented gravity fed exponential mixing and delivery system and apparatus useful for the administration of a drug in a precalculated manner to give constant therapeutic blood plasma levels in the patient.

The prior art discloses gravity fed intravenous (IV) administration systems for controlling the quantity of a single fluid to be delivered to the patient and/or to provide a controlled rate of flow thereof, as shown in U.S. Pat. Nos. 2,827,081, 2,853,069, 4,000,738 and 4,136,693. However, none of aforesaid systems include, nor make provision for, the mixing of two liquids generally or exponentially.

The prior art also discloses the insertion of mixing devices into an IV system for mixing two liquids or a solid and a liquid, to form a single solution of equal concentration during the total infusion period, as disclosed in U.S. Pat. No. 3,670,728 wherein two different liquids are packaged in a dual chamber flask separated by a septum capable of being upset to enable mixing of the two liquids, assisted by inletting air at the bottom of the flask and initiated by a pumping device for hand operation. U.S. Pat. No. 4,392,850 discloses an in-line transfer container containing a solid material to be intermixed in an IV solution, and serving as a mixing container, disposed below the IV solution container and provided with pierceable diaphragms at opposing ends to provide a fluid passageway for the incoming IV solution into the mixing container, wherein the flexible end wall thereof, is pumped to assist in the intermixing of the IV solution with the material in the mixing chamber, and subsequently piercing the opposing diaphragm to permit the fluid mixture to flow through the IV tubing to the patient. The use of this device involves multiple steps, requiring human intervention, and an excessive amount of time which may be life threatening in an emergency situation. U.S. Pat. No. 4,410,321 discloses a closed drug delivery system for separately storing and selectively mixing two components such as a drug and diluent under sterile conditions, comprising a compressible chamber containing a sterile liquid, a drug vial and a pierceable access means therebetween to create a pathway for the drug to flow into the compressible chamber which is positioned by hand manipulation to facilitate mixing of the drug and the liquid into a solution of uniform concentration for administration to the patient. However, none of aforesaid mixing systems effect exponential mixing nor are they gravity fed.

U.S. Pat. No. 4,424,056 discloses a parenteral administration system of delivering a fluid through a primary path, and a mixture of fluid and medicinal agent through a parallel path wherein the fluid passes through a formulation chamber containing an agent which dissolves in said fluid, and flows into the primary path for delivery to the patient at a controlled rate. The mixing that occurs in the formulation chamber is not exponential mixing.

U.S. Pat. No. 3,993,066 discloses a dual compartment burette chamber included in an administration set to provide both continuous intravenous (IV) solution and intermittant medicament to the patient. The burette chamber does not provide exponential mixing nor delivery.

U.S. Pat. No. 4,250,879 discloses the sequential administration of a plurality of medical liquids from separate sources (IV containers) at dual flow rates. This system does not provide exponential mixing nor delivery of a drug to give constant therapeutic blood plasma levels in the patient.

None of the aforesaid patents relate to the particular problems associated with the administration of certain drugs which require a constant plasma drug concentration, small variations thereof being either therapeutically ineffective or toxic. In either case, the results may be serious. This is particularly applicable in the intravenous administration of antiarrhythmic drugs such as lidocaine and other drugs that require a constant plasma drug concentration. Prior art methods used a loading dose and a maintenance infusion at a constant rate. This has been found to be suboptimal due to the production of wide variations in plasma drug concentrations early in therapy. Another prior art method used a series of precisely timed infusion rate changes, which merely minimized said variability and had the additional disadvantage of requiring human intervention at said timed intervals, which detracts from the ability to devote maximum attention to critical patients.

The best method theretofore utilized is the administration of an initial loading dose and an exponentially decreasing infusion rate obtained by approximation using mechanical constant rate infusion pumps and stepped decreases in the delivery rate. This method has the disadvantage of requiring frequent human intervention which is undesirable in a clinical setting.

An improvement on the above exponential infusion rate method utilizing a constant flow rate, is disclosed in *Annals of Internal Medicine*, 1984, Vol. 100, pp. 25–28, wherein a diluting solution of the drug, e.g. lidocaine, is mechanically pumped from a vented IV set into the base of a 20 ml multiple dose vial containing 1% lidocaine at a rate of 1 ml/min, said entering solution displacing solution at an equal rate from a needle inserted at the base of said vial. The resulting infusion concentration which decreases exponentially, is delivered to the patient. This apparatus has the disadvantage of requiring expensive equipment as well as cumbersome, such as a pump, which requires human intervention to start and stop said pump. There is a possibility of mechanical malfunction of the pump which would interfere with the drug infusion into the patient and its concomitant adverse effects such as insufficient drug therapy or toxic side effects due to increased drug infusion. The use of vented equipment is open to contamination from the air and a potential break in the sterility of the drug infusion.

None of the above cited art discloses a gravity fed, non-vented exponential mixing and delivery system and apparatus for the administration of a drug in a precalculated manner to 8ive constant therapeutic blood plasma levels in the recipient, at a constant delivery rate.

SUMMARY OF THE INVENTION

Accordingly, an object of the present invention is to provide an administration set capable of exponentially mixing and delivering a therapeutic agent in a precalculated manner to give constant blood plasma levels in the patient.

Another object of the present invention is to provide an exponential mixing chamber for use with an intravenous administration set.

Still another object of the present invention is to provide an exponential mixing and delivery apparatus for drug infusion at a constant delivery rate, without requiring frequent human intervention.

Additional objects, advantages and novel features of the invention will be set forth in the description which follows, and in part will become apparent to those skilled in the art upon examination of the following or may be learned by practice of the invention. The objects and advantages of the insertion may be realized and attained by means of the instrumentalities and combinations particularly pointed out in the appended claims.

To achieve the foregoing and other objects and in accordance with the present invention, as embodied and broadly described herein, the exponential mixing container for use with an intravenous administration set comprises a nonvented nondeformable mixing container provided with a vertical inlet conduit means extending downwardly from the top wall into said container, a piercing connecting means at the upper end of said inlet means for entering an IV solution container, said tip having a removable cover to ensure sterility, a vertical outlet conduit means extending upwardly from the bottom wall of said mixing container, the height differential between said conduit means operable to effect exponential mixing therein, a pierceable closure means at the lower end of said outlet means adapted to connect to conventional (standard) non-vented administration sets. Alternatively, the outlet conduit means in the exponential mixing container may be connected directly to a minidrip chamber, and IV tubing provided with a flow rate control valve, sealed side arm terminating in a leak proof seal, forming a prepackaged unit or kit. The exponential mixing container may additionally be provided with a piercable diaphragm on the top wall thereof for receiving a concentrated solution of the drug to be exponentially mixed and delivered to the patient.

It has now been found that the administration of a therapeutic agent in a precalculated manner to give constant therapeutic blood plasma levels in the patient, can be obtained quickly, efficiently, under sterile conditions, and in the absence of human intervention during the administration of the agent by using present novel non-vented gravity fed exponential mixing and delivery system which comprises the exponential mixing of a dilute solution of the drug or an isotonic solution which flows by gravity from a conventional IV container, through a coupling means, into a nonvented nondeformable mixing chamber, filled to capacity with a concentrated solution of said drug, said mixing container being provided with a vertical inlet conduit means and a vertical outlet conduit means at opposing ends, each conduit means extending into said mixing container at a height to provide a sufficient height differential to induce exponential mixing of the solutions, to effect an exponentially decreasing concentration of said drug during a constant infusion rate, flowing through said outlet conduit and into a conventional non-vented administration apparatus which may include a minidrip chamber to regulate the flow rate, and IV tubing provided with a flow rate control valve, and a sealed side-arm.

The non-vented gravity fed exponential mixing and delivery system, and apparatus generally comprises a non-vented nondeformable exponential mixing container filled to capacity with a concentrated solution of a drug, vertically aligned with a non-vented standard intravenous IV solution container, containing a drug-free solvent or diluent such as dextrose solution and/or a dilute solution of said drug, and provided with a pierceable closure means for coupling with the inlet means of the mixing container, for the gravity flow of the dilute solution from the IV solution container into said mixing container, said inlet means being provided with a connector means terminating in a piercing tip for engaging said pierceable closure means, said mixing container being provided with an inlet conduit means and an outlet conduit means on.opposing ends and extending into the mixing container, the height differential between said conduit means operable to effect exponential mixing, a minidrip chamber connected to said outlet conduit means to receive and regulate the flow of the exponentially decreasing concentration of said drug in the infusion per unit of time at a constant flow rate, to the patient by means of intravenous (IV) tubing provided with a control valve and sealed side-arm. Alternatively, the lower end of the outlet conduit means may be provided with a pierceable closure means adapted to connect to a standard nonvented administration set which may include a minidrip chamber, and IV tubing provided with a flow control valve and sealed side-arm.

More specifically, the non-vented, gravity fed exponential mixing and delivery system for the administration of a therapeutic agent in a precalculated manner to give constant therapeutic blood plasma levels in the recipient comprises an upper nonvented deformable intravenous container for containing a dilute solution of a therapeutic agent; a lower nonvented, nondeformable mixing container vertically aligned with the upper container for containing a concentrated solution of said agent; a coupling means between the upper and lower containers for the flow of solution from the upper container into a vertical inlet conduit means extending into the lower mixing container; a vertical outlet conduit means extending upwardly into the lower mixing container to provide a height differential between inlet and outlet conduit means for the exponential mixing of the dilute and concentrated solutions; said vertical outlet tube also extending downwardly into a minidrip chamber for the flow of exponentially decreasing concentrations of said therapeutic agent at a constant infusion rate and at a regulated flow rate to the patient.

The non-vented gravity fed exponential mixing and delivery apparatus in accordance with this invention comprises a non-vented deformable intravenous solution container containing a dilute solution of a drug or an isotonic solution, vertically aligned with a non-vented, nondeformable lower mixing container filled to capacity with a concentrated solution of said drug, a coupling means between the upper and lower containers to permit the gravity flow of the dilute solution into the concentrated solutions, said lower mixing container being provided with an inlet conduit means and an outlet conduit means on opposing ends, the height differential between said conduit means operable to effect exponential mixing therein, a minidrip chamber connected to said outlet conduit means to receive and regulate the flow of the exponentially decreasing concentration of said drug in the infusion per unit of time, at a constant flow rate, to the patient by means of intravenous tubing provided with a control valve and sealed side-arm.

The apparatus for implementing present novel gravity fed exponential mixing and delivery system is preferably in the form of an exponential mixing container for use with a standard intravenous administration set, comprising a nonvented, nondeformable mixing container provided with a vertical inlet conduit means extending downwardly from the top wall into said container and a vertical outlet conduit means extending upwardly from the bottom wall into said container, the height differential between said conduit means operable to effect exponential mixing in said mixing container, a means for coupling said inlet to a vertically aligned solution container for the gravity flow of liquid from the IV solution container (IV bag) into the mixing container, a pierceable closure means at the lower end of said outlet conduit means adapted to connect to conventional (standard) non-vented administration sets; or alternatively, said outlet conduit means is connected directly to a minidrip chamber, and IV tubing provided with a flow rate control valve, and a sealed sidearm, as part of the package.

The feasibility of using present novel exponential mixing container with conventional IV equipment presently on the market has many benefits and advantages. The standard nonvented, deformable IV bag containing 1 liter of dextrose and water or iostonic solution can be readily and easily connected to present novel exponential mixing container by removing the protective plastic cover from the piercing tip of the inlet connector and simply inserting said piercing tip in the pierceable closure means (diaphragm or plug) of the IV bag. It eliminates the necessity and expense of manufacturing new and complex equipment to deliver an infusion containing exponentially decreasing concentrations of a drug. It would also avoid possible new problems resulting from the use of the new equipment, such as possible seal leakage of the internal upper plug in the upper deformable container of the parent patent application Ser. No. 671,965, and possible deterioration (decomposition) of the drug such as lidocaine stored in the plastic deformable container. Present novel apparatus facilitates the use of varying concentrations of the drug to be administered, and is not limited to a single preformed and prepackaged concentration. It maintains the sterility and chemical stability of the drug in the preloaded syringe which is freshly added to the IV solution bag and optionally to the nondeformable exponential mixing container.

DESCRIPTION OF THE DRAWINGS

The following drawing more specifically describes present invention, wherein.

Figure 1:
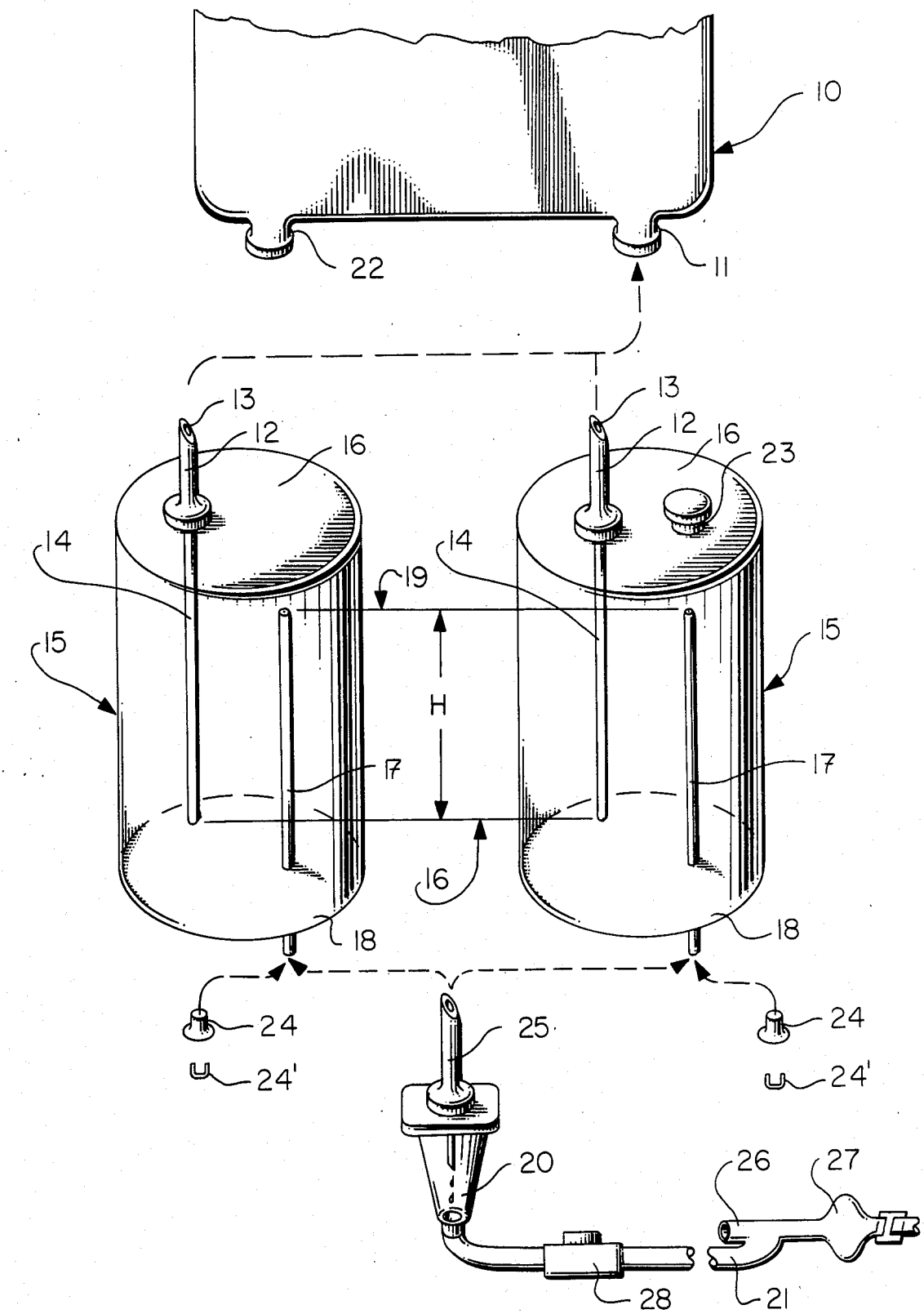
FIG. 1 is an elevational view of the exponential mixing and delivery system embodying the principles of this invention in operation.

In said drawing, the gravity fed exponential mixing and delivery system comprises a standard non-vented deformable IV solution container 10, containing a sterile diluting solution of a therapeutic agent or a solvent, provided with peirceable connector means 11, such as a standard pierceable female plug, adaptable for the insertion of male plug 12, provided with a peircing tip 13, at the upper end of inlet conduit means 14, of mixing container 15, filled to capacity with a concentrated sterile solution of said agent, to permit the gravity flow of liquid from the upper container 10, into lower mixing container 15, through inlet tube 14, depending from top wall 16, said inlet tube 14 extending downwardly into mixing container 15, to a height 16, such that the height differential H, between inlet tube 14, and outlet tube 17, integral with bottom wall 18, and extending upwardly to a height 19, is operable to effect exponential mixing in container 15. Said mixture of exponentially decreasing concentrations of the drug flows via outlet tube 17, into a minidrip chamber 20, at a regulated flow rate and through IV tubing 21, to the patient by opening a valve 28 for controlling the flow rate. The flow rate is regulated by the diameter of the flexible IV tubing. Exponential mixing of solutions commences in mixing container 15, upon opening outlet tube 17, to the flow of solution into the minidrip chamber 20, of the administration set. This ensures no mixing until this apparatus is connected to the patient and the infusion commences by opening flow rate valve 28.

Piercing tips 13 are covered with a removable plastic cover (not shown) to ensure sterility and prevent loss of solution prior to use.

Mixing container 15 is ductile but nondeformable and preferably made of clear plastic or glass.

Nondeformable exponential mixing container 15, may be further provided with an inlet means 23, in the top wall 16, for adding the drug in varying concentrations to the empty container 15, if desired. This provides greater versatility to the present novel exponential mixing and delivery system and apparatus for implementing said system. The mixing container 15 may be empty, or prepackaged and filled to capacity with a concentrated drug solution, prior to its connection to a non-vented IV administration set; or said exponential mixing container may be prepackaged as an integral unit with a nonvented IV administration set.

Deformable container 10, is in the form of a standard flexible IV bag sealed at the top and provided with a suitable suspension means for suspension from a bracket or other suitable support means (not shown).

Container 10 may be further provided with a pierceable inlet means 22, such as a rubber diaphragm, for adding the drug to the solution in the IV bag 10 to formulate a dilute solution of the drug, if desired.

The nondeformable mixing container 15 is provided with an airtight pierceable seal which may be in the form of a plug 24, or a plastic diaphragm 24', inserted into outlet tube 17, adaptable for the insertion of conventional non-vented administration sets by means of a hollow spike 25, leading into a minidrip chamber 20, connected to IV tubing 21, with sealed side-arm 26. Alternatively, the prepackaged mixing container may also include the administration set, i.e. the plug 24 or diaphragm 24' may be omitted, and the outlet tube 17 may be directly connected to the minidrip chamber 20, which is connected to IV tubing 21, provided with flow control valve 28, side-arm 26, and leak proof seal 27, to insure no flow prior to use, i.e. befdre connection to the infusion needle in the patient.

For example, a standard flexible IV bag 10 is filled with 1 liter of an aqueous solution containing 5% dextrose and 2 grams lidocaine, and the nondeformable container 15 is filled to capacity with 20 cc of dextrose water containing 1% lidocaine (200 mg lidocaine). The solution from bag 10 flows by gravity into container 15 through inlet tube 14 which is $\frac{1}{2}$" diameter 27 gauge, wherein the solutions are exponentially mixed, and flows out of container 15 through outlet tube 17 which is $1\frac{1}{2}$" diameter 22 gauge, into minidrip chamber 20, and is delivered to standard width IV tubing 21 at a rate of 1 drop/sec which is equal to 1 cc/min. A sufficient height differential of inlet tube 14 and outlet tube 17 ensures exponential mixing according to the equation:

$$R_t = Q\left[ C_d + (C_i - C_d)\frac{-Qt}{V} \right] \quad 1$$

wherein
$R_t$ = delivery rate gradient
$C_i$ = initial drug concentration of volume V in mixing chamber
$C_d$ = drug concentration of the diluting solution in flexible bag
Q = constant rate of delivery of diluent and removal of solution from the mixing chamber
t = time
e = exponential function.

According to this equation, this should deliver an infusion with a concentration of therapeutic agent which decreases exponentially from an initial rate of 10 mg/min to 2 mg/min with a half-life of 13.86 minutes.

While equation 1 is specific to the exponentially decreasing delivery of lidocaine from container 15 as induced by a solution from container 10 which is of lower concentration than the initial concentration, the invention can also be used to address the problem of an exponentially decreasing delivery rate of a solution from container 15 at a constant rate, as induced by a pure solvent from container 10, equation 1 then being altered as detailed by C. J. Morris and P. Morris in Separation Methods in Biochemistry. 2nd Edition, 1976; 103–4.

This invention is also applicable to other agents which are not governed by the same pharmacokinetic approach as lidocaine which would then follow the equations to obtain an instantaneous plasma drug concentration and to maintain it at a constant value, as derived by D. P. Vaughan and G. T. Tucker, in the *European Journal of Clinical Pharmacology*, 1976, Vol. 10, 433–40.

The height differential of outlet tube and inlet tube is effected by the volume and thus the design of the container itself. Generally, for containers of small capacity, such as discussed above, as long as the end of each tube is positioned at the extreme opposite end to the tubes' point of entry without restricting flow, the criteria of the design is met. To be more specific, the laws of diffusion/mass transport are governed by the rate of mass transfer.

This novel and useful invention provides an exponential mixing and delivery system and apparatus for the administration of a therapeutic agent to yield rapidly attained and maintained constant therapeutic plasma levels, by simply connecting the exponential mixing container to a standard IV solution bag suspended from a suitable support, connecting the outlet tube of said mixing container to the minidrip chamber of an IV administration kit, which leads into the patient; or connecting a prepackaged unit of the nonvented mixing container integral with a nonvented administration set to a standard IV bag suspended from a suitable support, administering one bolus injection of 1 mg/kg body weight, through side-arm 26 at the start of said infusion or shortly thereafter. The infusion starts immediately and requires no other human intervention until the contents are exhausted. The exponentially decreasing amount of therapeutic agent insures a constant concentration of therapeutic agent in the blood plasma, thereby avoiding toxicity due to an overdose, or ineffectual drug therapy due to an underdose. This is of particular importance in emergency or critical clinical situations such as in patients with cardiac failure or with concurrent decreased hepatic or renal function.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

I claim:

1. A non-vented, gravity fed exponential mixing and delivery system for the administration of a therapeutic agent in a precalculated manner to give constant therapeutic blood plasma levels in the recipient which comprises
    an upper non-vented deformable intravenous container for containing a dilute solution of a therapeutic agent,
    a lower non-vented, nondeformable mixing container vertically aligned with the upper container for containing a concentrated solution of said agent,
    a coupling means between the upper and lower containers for the gravity flow of solution from the upper container directly into a vertical inlet conduit means extending downwardly into the lower mixing container, the end of said vertical inlet conduit means extending to a point adjacent the bottom of the mixing container at the extreme opposite end of its point of entry without restricting flow,
    a vertical outlet conduit means extending upwardly from the bottom of the mixing container, the end of said vertical outlet conduit means extending to a point adjacent the top of the mixing container at the extreme opposite end of its point of entry without restricting flow to provide a height differential between inlet and outlet conduit means for the exponential mixing of the dilute and concentrated solutions, said conduit means being non-aligned in parallel,
    said vertical outlet conduit means tube also extending downwardly into a minidrip chamber for the flow of exponentially decreasing concentrations of said therapeutic agent at a constant infusion rate and at a regulated flow rate to the patient by means of intravenous tubing, provided with a control valve for simultaneously initiating the exponential mixing in said mixing container and the infusion into the patient.

2. A non-vented gravity fed exponential mixing and delivery apparatus comprising a non-vented deformable upper intravenous (IV) container containing a drug free solvent or diluent or dilute solution of the drug, vertically aligned with a non-vented, nondeformable exponential mixing container filled to capacity with a concentrated solution of said drug, a pierceable outlet means in the upper IV container for coupling with an inlet means in the lower mixing container for the gravity flow of the dilute solution from the upper container directly into the lower mixing container, said lower mixing container being provided with a top inlet conduit means and a bottom outlet conduit means on opposing ends, said inlet means being provided with a connector means for coupling with the pierceable outlet means of the upper container, the ends of the inlet and outlet conduit means within the mixing container extending to a point adjacent the respective bottom and top of said mixing container at the extreme opposite ends of each conduit means' point of entry without restricting flow, the height differential between said conduit means operable to effect exponential mixing in said mixing container, said conduit means being non-aligned in parallel a minidrop chamber connected to said outlet conduit means to receive and regulate the flow of the exponentially decreasing concentration of said drug in the infusion per unit of time, at a constant flow rate, to the patient, by means of intravenous (IV) tubing, provided with a control valve to simultaneously initiate the exponential mixing in the mixing container and the infusion into the patient.

3. An exponential mixing container for use with an intravenous administration set, comprising a non-vented, nondeformable mixing container provided with a vertical inlet conduit means extending downwardly from the top wall into said container, and a vertical outlet conduit means extending upwardly from the bottom wall into said container said conduit means being non-aligned in parallel, the ends of the inlet and outlet conduit means within the mixing container extending to a point adjacent the respective bottom and top of said mixing container at the extreme opposite end of each conduit means' point of entry without restricting flow, the height differential between said conduit means operable to effect exponential mixing in said mixing container, a means for coupling said inlet to an IV solution container, a pierceable closure means at the lower end of said outlet conduit means adapted to connect to conventional non-vented administration sets.

4. The exponential mixing container according to claim 3, wherein said outlet conduit means is connected directly to a minidrip chamber, IV tubing, sealed sidearm, and terminating in a leak proof seal, as a prepackaged unit.

5. The exponential mixing container according to claim 3 or 4, additionally provided with an inlet means on the top wall thereof for receiving a concentrated solution of the drug to be exponentially mixed and delivered to the patient.

6. The exponential mixing container according to claim 3 or 4, wherein the upper end of the inlet conduit means is provided with a connector having a piercing tip adapted to enter an IV solution container, said tip having a removable cover to ensure sterility, 7. The system according to claim 1, wherein the upper deformable container is filled with a drug fee solvent.

8. The exponential mixing container according to claim 3 or 4, which is filled to capacity with a concentrated solution of a drug.

9. The apparatus according to claim 2, wherein the exponential mixing container is additionally provided with an inlet means on the top wall thereof for receiving a concentrated solution of the drug to be exponentially mixed and delivered to the patient.

10. The apparatus according to claim 2, wherein the upper end of the inlet conduit means of the mixing container is provided with a connector having a piercing tip adapted to enter the IV solution container, said tip having a removable cover to ensure sterility.

* * * * *